(12) United States Patent
Cassivi et al.

(10) Patent No.: US 9,005,275 B2
(45) Date of Patent: Apr. 14, 2015

(54) METHODS FOR REPLACING A CIRCUMFERENTIAL SEGMENT OF AN ESOPHAGUS

(71) Applicant: Mayo Foundation for Medical Education and Research, Rochester, MN (US)

(72) Inventors: Stephen D. Cassivi, Rochester, MN (US); Dennis A. Wigle, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 13/672,501

(22) Filed: Nov. 8, 2012

(65) Prior Publication Data
US 2013/0131827 A1    May 23, 2013

Related U.S. Application Data

(60) Provisional application No. 61/561,496, filed on Nov. 18, 2011.

(51) Int. Cl.
*A61F 2/04* (2013.01)

(52) U.S. Cl.
CPC ............. *A61F 2/04* (2013.01); *A61F 2002/044* (2013.01); *A61F 2250/0063* (2013.01)

(58) Field of Classification Search
CPC ......... A61F 2/04; A61F 2/02; A61F 2002/07; A61F 2002/072; A61F 2002/075; A61F 2002/077; A61F 2002/044; A61F 2002/848

USPC ................ 623/1.15, 1.36, 1.44, 11.11, 23.64, 623/23.69, 23.7, 66.1

See application file for complete search history.

(56) References Cited

U.S. PATENT DOCUMENTS

| | | | |
|---|---|---|---|
| 4,655,771 | A | 4/1987 | Wallsten |
| 4,728,328 | A | 3/1988 | Hughes et al. |
| 6,241,757 | B1 | 6/2001 | An et al. |
| 6,241,774 | B1 | 6/2001 | Shimizu |
| 6,305,436 | B1 | 10/2001 | Andersen et al. |
| 7,121,999 | B2 | 10/2006 | Abraham et al. |
| 7,699,886 | B2 | 4/2010 | Sugimoto |
| 7,727,271 | B2 | 6/2010 | Kujawski et al. |
| 7,766,959 | B2 | 8/2010 | DiMatteo et al. |
| 7,828,833 | B2 | 11/2010 | Haverkost et al. |
| 7,993,410 | B2 | 8/2011 | Shin et al. |
| 2003/0129751 | A1 | 7/2003 | Grikscheit et al. |
| 2007/0166396 | A1 | 7/2007 | Badylak et al. |

OTHER PUBLICATIONS

Yasumichi Yamamoto et al. "Intrathoracic Esophageal Replacement with a Collagen-Sponge-Silicone Double Layer Tube: Evaluation of Omental-Pedicle Wrapping and Prolonged Placement of an Inner Stent", Mar. 2000, ASAIO Journal, v46, pp. 734-739.*

(Continued)

*Primary Examiner* — Randy Shay
(74) *Attorney, Agent, or Firm* — Fish & Richardson P.C.

(57) ABSTRACT

This document provides methods and materials that can be used to replace a circumferential segment of an esophagus. For example, methods and materials that can be used to provide a tubular connection from one stump end of an esophagus to another stump end of the esophagus are provided.

5 Claims, 7 Drawing Sheets

(56) References Cited

OTHER PUBLICATIONS

Stoeckel et al., "A survey of stent designs," Min. Invas. Ther. & Allied Technol., vol. 11(4), 2002, pp. 137-147.

Zhi et al., "Experimental reconstruction of dog's esophagus with biotype artificial esophagus," Chinese Journal of Digestive Diseases, vol. 4, 2003, pp. 168-173.

Doede et al., "Unsuccessful Alloplastic Esophageal Replacement with Porcine Small Intestinal Submucosa," Artificial Organs, vol. 33(4), 2009, pp. 328-333.

Badylak et al., "Resorbable Bioscaffold for Esophageal Repair in a Dog Model," Journal of Pediatric Surgery, vol. 35 (7), Jul. 2000, pp. 1097-1103.

Yamamoto et al., "Experimental Replacement of the Thoracic Esophagus with a Bioabsorbable Collagen Sponge Scaffold Supported by a Silicone Stent in Dogs," ASAIO Journal, 1999, pp. 311-316.

Saxena et al., "Esophagus tissue engineering: in situ generation of rudimentary tubular vascularized esophageal conduit using the ovine model," Journal of Pediatric Surgery, vol. 45, Jan. 2010, pp. 859-864.

Nieponice et al., "Reinforcement of Esophageal Anastomoses With an Extracellular Matrix Scaffold in a Canine Model," Ann. Thorac. Surg., vol. 82, 2006, pp. 2050-2058.

Liang et al., "Polyester Connecting Ring Improves Outcome in Nitinol Composite Artificial Esophagus," ASAIO Journal, 2009, pp. 514-518.

Fukushima et al., "Seven-year follow-up study after the replacement of the esophagus with an artificial esophagus in the dog," Surgery, vol. 93(1), 1983, pp. 70-77.

Yamamoto et al., "Inthrathoracic Esophageal Replacement with a Collagen Sponge-Silicone Double Layer Tube: Evaluation of Omental-Pedicle Wrapping and Prolonged Placement of an Inner Stent," ASAIO Journal, 2000, pp. 734-739.

Dobrzanski et al., "Constructional model of internal oesophageal prosthesis," International Scientific Journal, vol. 42 (2), Apr. 2010, pp. 69-76.

Nakase et al., "Intrathoracic esophageal replacement by in situ tissue-engineered esophagus," The Journal of Thoracic and Cardiovascular Surgery, vol. 136(4), Oct. 2008, pp. 850-859.

\* cited by examiner

METHODS FOR REPLACING A CIRCUMFERENTIAL SEGMENT OF AN ESOPHAGUS

CROSS-REFERENCE TO RELATED APPLICATIONS

This application claims the benefit of U.S. Provisional Application Ser. No. 61/561,496, filed Nov. 18, 2011. The disclosure of the prior application is considered part of (and is incorporated by reference in) the disclosure of this application.

BACKGROUND

1. Technical Field

This document relates to methods and materials involved in replacing a circumferential segment of an esophagus. For example, this document relates to methods and materials that can be used to provide a tubular connection from one stump end of an esophagus to another stump end of the esophagus.

2. Background Information

Patients with esophageal cancer or high grade dysplasia may undergo an esophagectomy to remove of an entire cross-sectional segment of the patient's esophagus. In such cases, the patient's stomach may be elevated to close the created gap in the esophagus or a tubular replacement such as a colonic or small intestine segment may be used to bridge the created gap. Both options appear to result in limited success.

SUMMARY

This document provides methods and materials that can be used to replace a circumferential segment of an esophagus. For example, this document provides methods and materials that can be used to provide a tubular connection from one stump end of an esophagus to another stump end of the esophagus. As described herein, an esophageal replacement device can be implanted into a patient to bridge a gap between two stump ends of a patient's esophagus. In some cases, an esophageal replacement device provided herein can be implanted into a patient in a manner such that the patient does not suffer from subsequent esophageal stenosis. In some cases, an esophageal replacement device provided herein can include non-biological material that can be removed from the patient after a period of time. For example, an esophageal replacement device provided herein can include a non-biological layer and a biological or bioabsorbable layer. In such cases, the non-biological layer can be separated from and endoscopically or surgically removed from the patient at a particular time post implantation (e.g., after sufficient cellular in-growth occurs to support a functional esophagus).

In general, one aspect of this document features an esophageal replacement device for replacing a circumferential segment of an esophagus. The device comprises, or consists essentially of, (a) a first layer comprising a distal end region configured to be inserted into the channel of a lower stump end of the esophagus, a proximal end region configured to be inserted into the channel of an upper stump end of the esophagus, and a central region located between the distal end region and the proximal end region, wherein the first layer defines a channel configured to allow for food transit, wherein at least a portion of the distal end region comprises a stent ring structure, wherein at least a portion of the proximal end region comprises a stent ring structure, and wherein at least a section of the central region lacks a stent ring structure, and (b) a second layer located in an outer position relative to the first layer, wherein the second layer comprises a distal end portion configured to be proximate to or to extend over an outer surface of the lower stump end of the esophagus, a proximal end portion configured to be proximate to or to extend over an outer surface of the upper stump end of the esophagus, and a central portion located between the distal end portion and the proximal end portion. The distal end region of the first layer can extend past the distal end portion of the second layer. The proximal end region of the first layer can extend past the proximal end portion of the second layer. The distal end region of the first layer can extend past the distal end portion of the second layer, and wherein the proximal end region of the first layer extends past the proximal end portion of the second layer. The first layer can be longer than the second layer. The stent ring structure of the distal end region can extend past the distal end portion of the second layer. The stent ring structure of the proximal end region can extend past the proximal end portion of the second layer. The stent ring structure of the distal end region can extend past the distal end portion of the second layer, and wherein the stent ring structure of the proximal end region can extend past the proximal end portion of the second layer. The distal end portion can be configured to be attached to the inner layer. The distal end portion can be attached to the inner layer. The proximal end portion can be configured to be attached to the inner layer. The proximal end portion can be attached to the inner layer. The distal end portion can be configured to be attached to the lower stump end of the esophagus. The distal end portion can be configured to be sutured to the lower stump end of the esophagus. The proximal end portion can be configured to be attached to the upper stump end of the esophagus. The proximal end portion can be configured to be sutured to the upper stump end of the esophagus. At least a portion of the first layer can be directly attached to the second layer. At least a portion of the first layer can be indirectly attached to the second layer. At least a portion of the first layer can be removably attached to the second layer. The first layer can comprise a strut that extends from the distal end region to the proximal end region, wherein the strut can be configured to increase the patency of the channel. The strut can be coil shaped. The strut can define a lumen capable of housing material. The strut can define an opening configured to allow the material to be released from the lumen. The strut can define two or more openings configured to allow the material to be released from the lumen. The first layer can comprise a ring structure attached to the strut. The ring structure can define a lumen capable of housing material. The ring structure can define an opening configured to allow the material to be released from the lumen. The ring structure can define two or more openings configured to allow the material to be released from the lumen. The first layer can comprise two or more ring structures attached to the strut. Each of the two or more ring structures can define a lumen capable of housing material. Each of the two or more ring structures can define an opening configured to allow the material to be released from the lumen. Each of the two or more ring structures can define two or more openings configured to allow the material to be released from the lumen. The ring structure of the distal end region and the ring structure of the proximal end region can comprise more radial force than the strut. The first layer can comprise two or more struts that extend from the distal end region to the proximal end region, wherein the struts can be configured to increase the patency of the channel. The ring structure of the distal end region and the ring structure of the proximal end region can comprise more radial force than the two or more struts. The first layer can comprise two or more ring structures, wherein each of the ring structures can be attached to at least two of the two or more struts. The first layer can be substantially fluid impermeable. The first layer can be fluid impermeable. An inner surface of the first layer can comprise a coating. The coating can be a hydrophobic coating. The first layer can comprise polytetrafluoroethylene. The second layer can be configured to allow cellular in-growth. The second layer can comprise matrix material. The matrix material can be decellularized esophagus, decellularized bowel, or a biological matrix. The second layer can comprise mesenchymal stem cells.

In another aspect, this document features a method for replacing a circumferential segment of an esophagus removed from a mammal with an esophageal replacement device. The esophageal replacement device comprises, or consists essentially of, (a) a first layer comprising a distal end region having a stent ring structure and a proximal end region having a stent ring structure, and (b) a second layer located in an outer position relative to the first layer, wherein the second layer comprises a distal end portion and a proximal end portion. The method comprises, or consists essentially of, (i) inserting at least a portion of the distal end region into a channel of a lower stump end of the esophagus, (ii) inserting at least a portion of the proximal end region into a channel of a upper stump end of the esophagus, (iii) positioning at least a portion of the distal end portion proximate to or over an outer surface of the lower stump end of the esophagus, and (iv) positioning at least a portion of the proximal end portion proximate to or over an outer surface of the upper stump end of the esophagus. The mammal can be a human. The method can comprise suturing the distal end region to the lower stump end of the esophagus. The method can comprise suturing the proximal end region to the upper stump end of the esophagus. The method can comprise suturing the distal end portion to the lower stump end of the esophagus. The method can comprise suturing the proximal end portion to the upper stump end of the esophagus. The method can comprise applying paste to the second layer. The paste can comprise angiogenic factor or a growth factor. The method can comprise removing the first layer from the mammal after cellular in-growth into the second layer occurs. The first layer can be longer than the second layer.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

This document provides methods and materials that can be used to replace a circumferential segment of an esophagus. For example, this document provides methods and materials that can be used to provide a tubular connection from one stump end of an esophagus to another stump end of the esophagus. As described herein, an esophageal replacement device can be implanted into a patient to bridge a gap between two stump ends of a patient's esophagus.

In some cases, an esophageal replacement device provided herein can include a first layer and a second layer. The first layer can be configured to have one end configured to be inserted into the channel of one stump end of the esophagus and another end configured to be inserted into the channel of the other stump end of the esophagus. One or both sections of the first layer to be inserted into the stump ends can include a ring stent structure. The ring stent structure can anchor the device and provide radial force to increase patency. In some cases, the first layer can include one or more struts configured to increase patency.

The second layer can be located in an outer position relative to the first layer. In some cases, the second layer can be configured to have one end configured to be extended over an outer surface of one stump end of the esophagus and another end configured to be extended over an outer surface of the other stump end of the esophagus. The portions extending over the stump ends can be attached to (e.g., sutured to) the esophagus.

In some cases, an esophageal replacement device provided herein can include a third layer. The third layer can be located in an outer position relative to second layer. In such cases, the third layer can be configured to have one end configured to be extended over an outer surface of one stump end of the esophagus and another end configured to be extended over an outer surface of the other stump end of the esophagus. The portions extending over the stump ends can be attached to (e.g., sutured to) the esophagus. In such cases, the portions of the second layer that extend over the stump ends can be attached or unattached to the esophagus.

An esophageal replacement device provided herein can be implanted into a patient in a manner such that the patient does not suffer from subsequent esophageal stenosis. In some cases, an esophageal replacement device provided herein can be used in a manner that avoids leakage, stricture, failure of tissue regrowth, obstruction, migration, and/or displacement.

Figure 1:
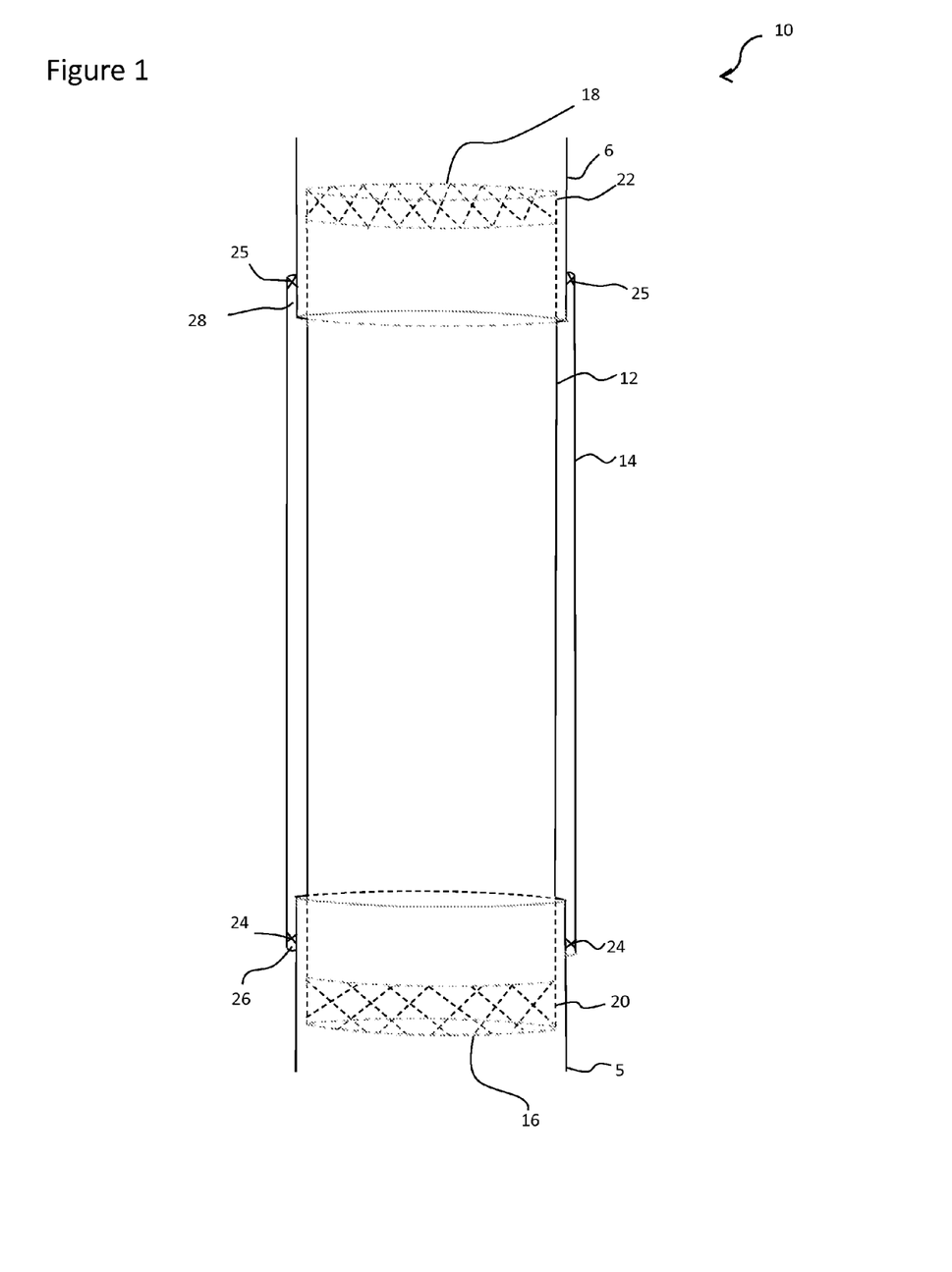
FIG. 1 is a side view of an esophageal replacement device in accordance to one embodiment provided herein. The forward portion of outer layer 14 is not shown to provide a better view of the other components.

With respect to FIG. 1, device 10 includes first layer 12 and second layer 14. First layer 12 can define a lumen and can include distal end region 16 and proximal end region 18. The lumen can have any appropriate diameter. For example, the diameter of the lumen can be between about 5 mm and about 40 mm. Distal end region 16 can be configured to be inserted into the channel of one stump end 5 of an esophagus. Distal end region 16 can be inserted into the channel any appropriate distance (e.g., between about 0 mm and about 50 mm). Proximal end region 18 can be configured to be inserted into the channel of another stump end 6 of an esophagus. Proximal end region 18 can be inserted into the channel any appropriate distance (e.g., between about 0 mm and about 50 mm). In some cases, a ring structure can be attached to one or both stumps such that there is no overhang (e.g., the edge of the stump end can be sewn to a ring structure). In such cases, second layer 14 can be longer than first layer 12 to prevent leakage.

In some cases, distal end region 16 can include a ring stent structure 20. Ring stent structure 20 can be completely inserted into the channel of one stump end 5 of an esophagus. In some cases, ring stent structure 20 can be partially inserted into the channel of one stump end 5 of an esophagus (not shown). In some cases, proximal end region 18 can include a ring stent structure 22. Ring stent structure 22 can be completely inserted into the channel of one stump end 6 of an esophagus. In some cases, ring stent structure 22 can be partially inserted into the channel of one stump end 6 of an esophagus (not shown). Ring stent structures 20 and 22 can be composed of any appropriate material and can have any appropriate ring configuration. For example, materials such as stainless steel, shape-memory alloys (e.g., Nitinol), tantalum alloy, Elgiloy, cobalt-chromium alloy, or other alloys, titanium, carbon fiber, polymers (e.g., polyethylene, polypropylene, polyurethane, polyester, etc.), or other materials or combinations of materials with sufficient strength and elasticity, or combinations thereof can be used to make a ring stent structure. In some cases, a ring stent structure or structures can be biodegradable or composed of biodegradable materials. Examples of biodegradable materials include, without limitation, polyesters, polycarbonates, poly-L-lactic acid (PLLA), polyglycolic acid (PGA), poly (D, L-lactide/glycolide) copolymer (PDLA), polycaprolactone (PCL), polydioxanone, bacterial-derived polymers, corrodible metals, and combinations thereof. In some cases, ring stent structures 20 and 22 can have a configuration similar to those described elsewhere (e.g., Stoeckel et al., *Min. Invas. Ther. & Allied Technol.*, 11(4):137-147 (2002) and U.S. Pat. Nos. 6,305,436, 4,655,771, 6,241,757, and 7,993,410). The length of ring stent structures 20 and 22 can be between about 10 mm and about 50 mm. In some cases, spars, barbs, or the like may be incorporated into the geometry of ring stent structures 20 and 22, in order to reduce migration following implantation.

First layer 12 can have any appropriate length depending on the size of the gap to be bridged. For example, first layer 12 can be between about 1 cm and about 25 cm. In some cases, first layer 12 can be substantially fluid impermeable or can be composed of a substantially fluid impermeable material. Examples of substantially fluid impermeable materials include, without limitation, polytetrafluoroethylene (PTFE; Teflon), expanded PTFE with or without fluorinated ethylene propylene (FEP) or other polymeric coating, Gore-Tex, polyurethane, polypropylene, silicone, Dacron, polyester, other polymers, and combinations thereof.

In some cases, each component of an esophageal replacement device provided herein can be composed of biodegradable material. In such cases, the esophageal replacement device can remain in the mammal without removing any of its components since it will degrade over time.

Second layer 14 can define a lumen and can include distal end portion 26 and proximal end portion 28. The lumen can have any appropriate diameter. For example, the diameter of the lumen can be between about 6 mm and about 45 mm. Distal end portion 26 can be configured to extend over an outer surface of one stump end 5 of an esophagus. Distal end portion 26 can be configured to extend over the outer surface of one stump end any appropriate distance (e.g., between about 10 mm and about 50 mm). In some cases, distal end portion 26 can be configured to be in flush alignment with outer surface of one stump end 5 of an esophagus. In some cases, distal end portion 26 can be configured to be proximate (e.g. within about 1 cm) of one stump end 5 of an esophagus. Proximal end portion 28 can be configured to extend over an outer surface of another stump end 6 of an esophagus. Proximal end portion 28 can be configured to extend over the outer surface of one stump end any appropriate distance (e.g., between about 6 mm and about 45 mm). In some cases, proximal end portion 28 can be configured to be in flush alignment with outer surface of one stump end 5 of an esophagus. In some cases, proximal end portion 28 can be configured to be proximate (e.g. within about 1 cm) of one stump end 5 of an esophagus. In some cases, distal end portion 26 can include an attachment location 24, and proximal end portion 28 can include an attachment location 25. Attachment locations 24 and 25 can be configured in a manner that allows the second layer to be sutured or clipped to the stump ends of the esophagus.

Second layer 14 can have any appropriate length depending on the size of the gap to be bridged. For example, second layer 14 can be between about 1 cm and about 30 cm. In some cases, second layer 14 can be shorter than first layer 12. In some cases, second layer 14 can be longer than first layer 12. In some cases, second layer 14 can be composed of a matrix material. Examples of matrix materials include, without limitation, decellularized esophagus, decellularized bowel, or other decellularized tissue (e.g., skin, pericardium, scalp, bladder, etc.) from human, porcine, bovine, ovine, or other mammalian sources; composite grafts containing collagen, elastin, fibronectin, or other extracellular matrix materials, and other biologic or non-biologic materials and combinations thereof.

Figure 2:
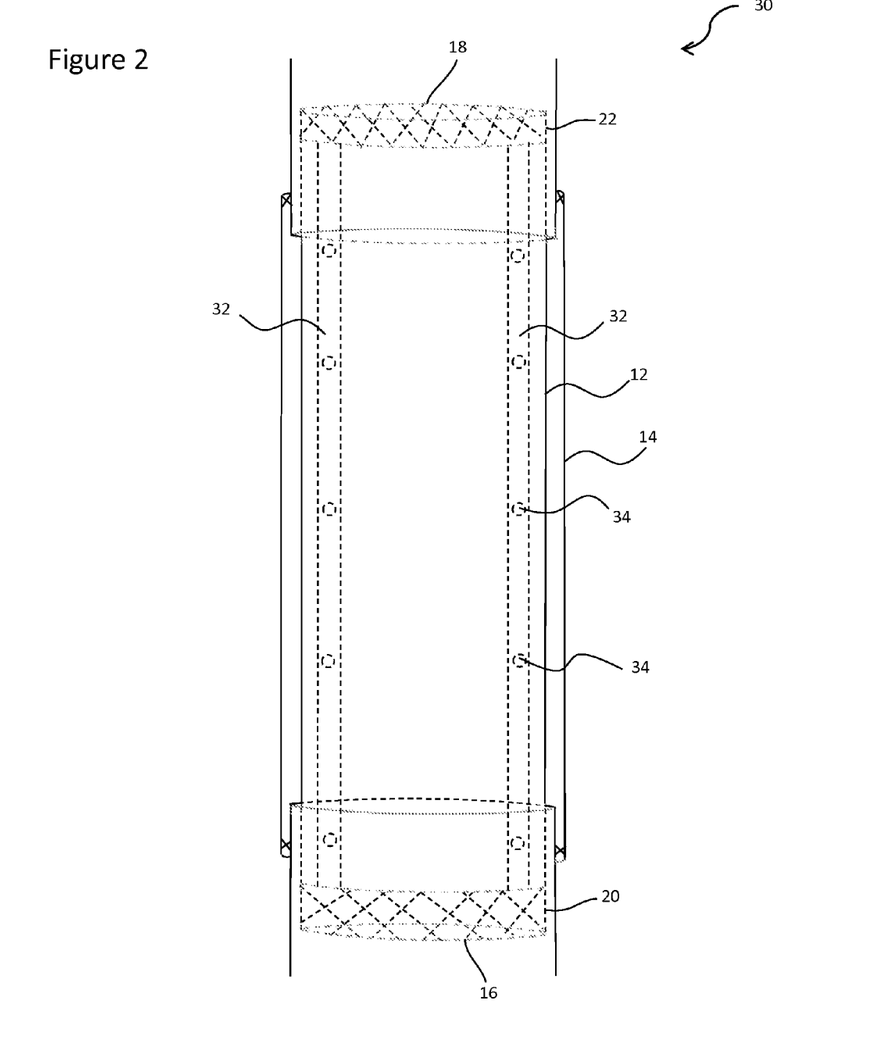
FIG. 2 is a side view of an esophageal replacement device containing struts in accordance to one embodiment provided herein. The forward portion of outer layer 14 is not shown to provide a better view of the other components.
Figure 3:
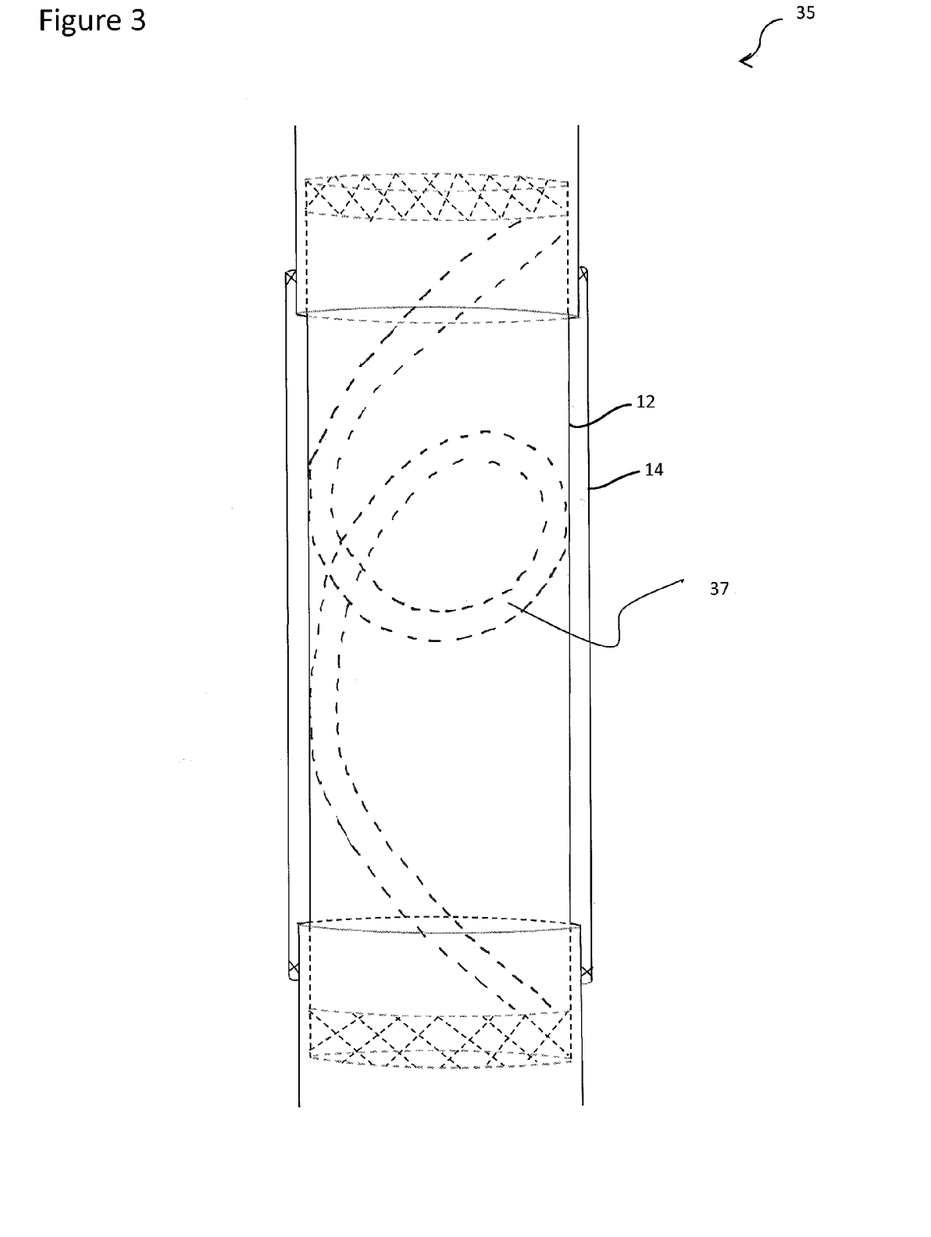
FIG. 3 is a side view of an esophageal replacement device containing a coiled strut in accordance to one embodiment provided herein. The forward portion of outer layer 14 is not shown to provide a better view of the other components.
Figure 4:
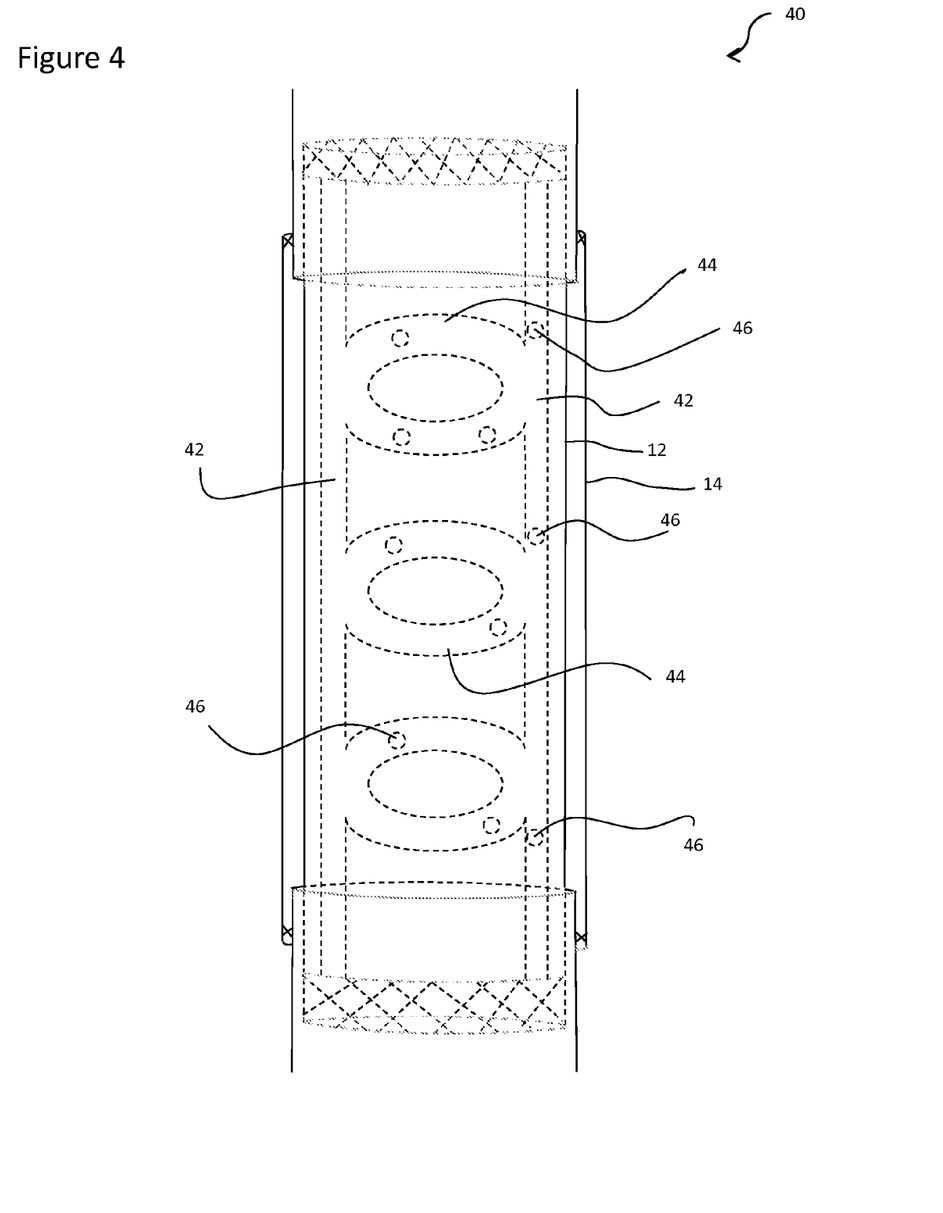
FIG. 4 is a side view of an esophageal replacement device containing rings and struts in accordance to one embodiment provided herein. The forward portion of outer layer 14 is not shown to provide a better view of the other components.

With reference to FIG. 2, device 30 can include first layer 12 and second layer 14. First layer 12 can include struts 32. Struts 32 can extend in a direction from proximal end region 18 toward distal end region 16. In some cases, struts 32 can extend the entire length of first layer 12. In some cases, struts 32 can extend from ring structure 22 to ring structure 20. A device provided herein can include any appropriate number of struts (e.g., one, two, three, four, five, six, seven, eight, nine, ten, or more struts). In some cases, struts 32 can define a lumen and can include one or more openings 34 (e.g., one, two, three, four, five, six, seven, or more openings). The lumen can be configured to house any appropriate material such as cells (e.g., mesenchymal stem cells, induced pluripotent stem cells, epithelial cells, or any epithelial or mesenchymal derivative cells, (embryonic, fetal, or adult)), growth factors (e.g., FGF, EGF, NGF, or TGF-β), angiogenic factors (e.g., VEGF, angiopoietins, or MMP's), cytokines, lysates (e.g., esophageal, small or large bowel, platelet), or combinations thereof. Struts 32 can have any appropriate configuration. For example, as shown in FIG. 2, struts 32 can have a generally linear configuration. In some cases, a lattice or any other suitable configuration can be used. In some cases, a first layer 12 can include one or more struts having a coil configuration as shown, for example, in FIG. 3 (e.g., strut 37). With reference to FIG. 4, device 40 can include first layer 12 and second layer 14. First layer 12 can include struts 42 and rings 44. Struts 42, rings 44, or both can define a lumen and can include one or more openings 46 (e.g., one, two, three, four, five, six, seven, or more openings). The lumen of struts 42, rings 44, or both can be configured to house any appropriate material such as cells (e.g., mesenchymal stem cells, induced pluripotent stem cells, epithelial cells, or any epithelial or mesenchymal derivative cells), growth factors (e.g., FGF, EGF, NGF, or TGF-β), angiogenic factors (e.g., VEGF, angiopoietins, or MMP's), cytokines, lysates (e.g., esophageal, small or large bowel, platelet), or combinations thereof.

The lumen of the struts or rings or both can be pre-loaded with any appropriate material. Openings 46 can be sealed until the device is deployed. Upon device deployment, the seal can be removed, allowing release of the material over time through openings 46. In some cases, the material can be loaded in vivo. For example, a one-way valve or other appropriate mechanism located on the proximal end of first layer 12, ring stent structure 20, or other appropriate location could be accessed endoscopically and engaged with a needle, catheter, or other suitable device to deposit cells, growth factors and other materials into the lumen. In some cases, struts or rings can include a drug-eluting coating (e.g., growth inhibiting drugs to prevent stenosis such as paclitaxel, sirolimus, everolimus, or zotarolimus or other drugs).

Figure 5:
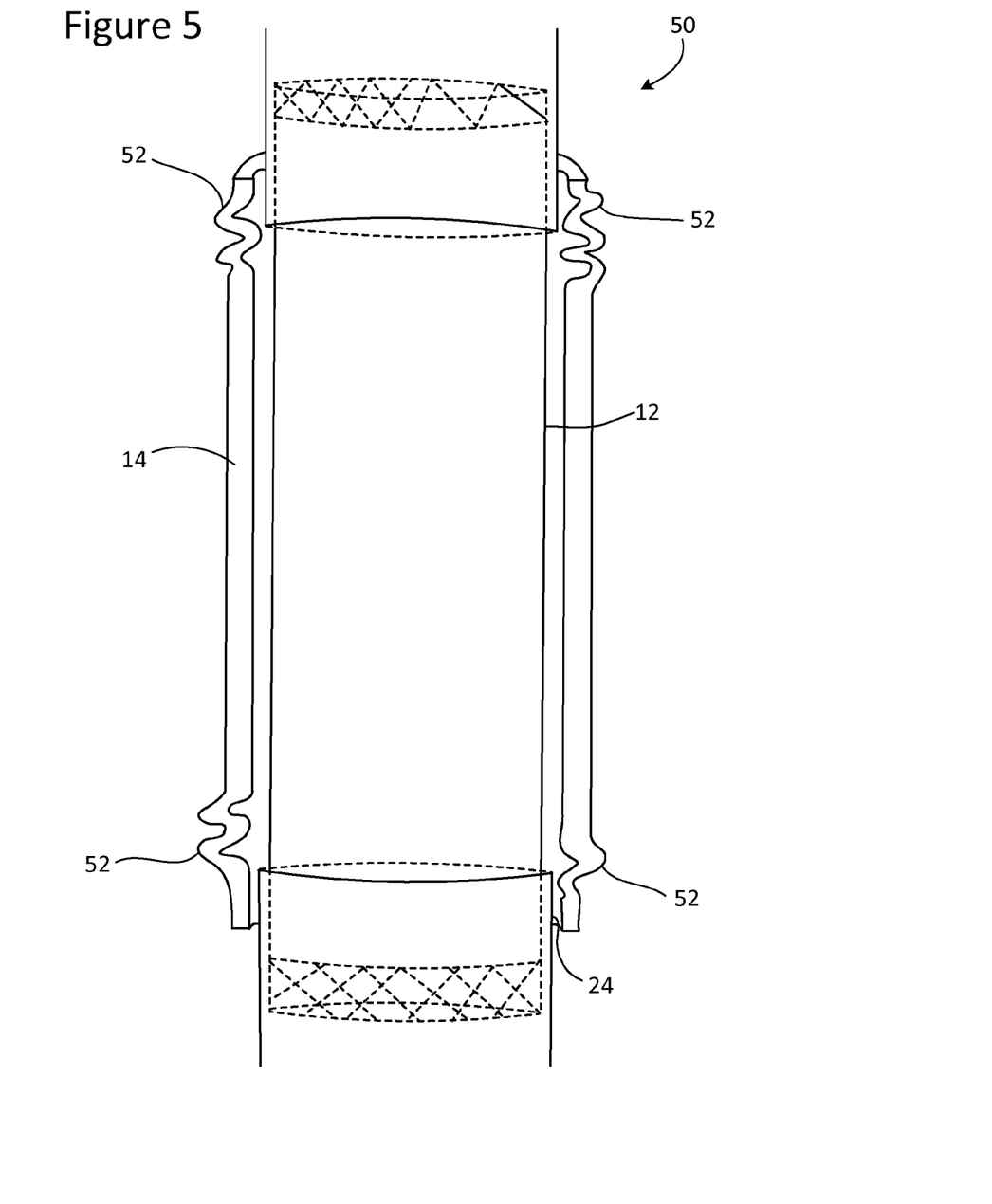
FIG. 5 is a side view of an esophageal replacement device having an outer layer with extra material in accordance to one embodiment provided herein. The forward portion of outer layer 14 is not shown to provide a better view of the other components.

With reference to FIG. 5, device 50 can include first layer 12 and second layer 14. Second layer 14 can include extensions 52. Extensions 52 can provide additional second layer material in an area near attachment location 24. Extensions 52 can reduce the chance of leakage and/or prevent or reduce tension in order to maintain connection of second layer 14 to a stump end of an esophagus in case of contraction of one or both of the stump ends.

Figure 6:
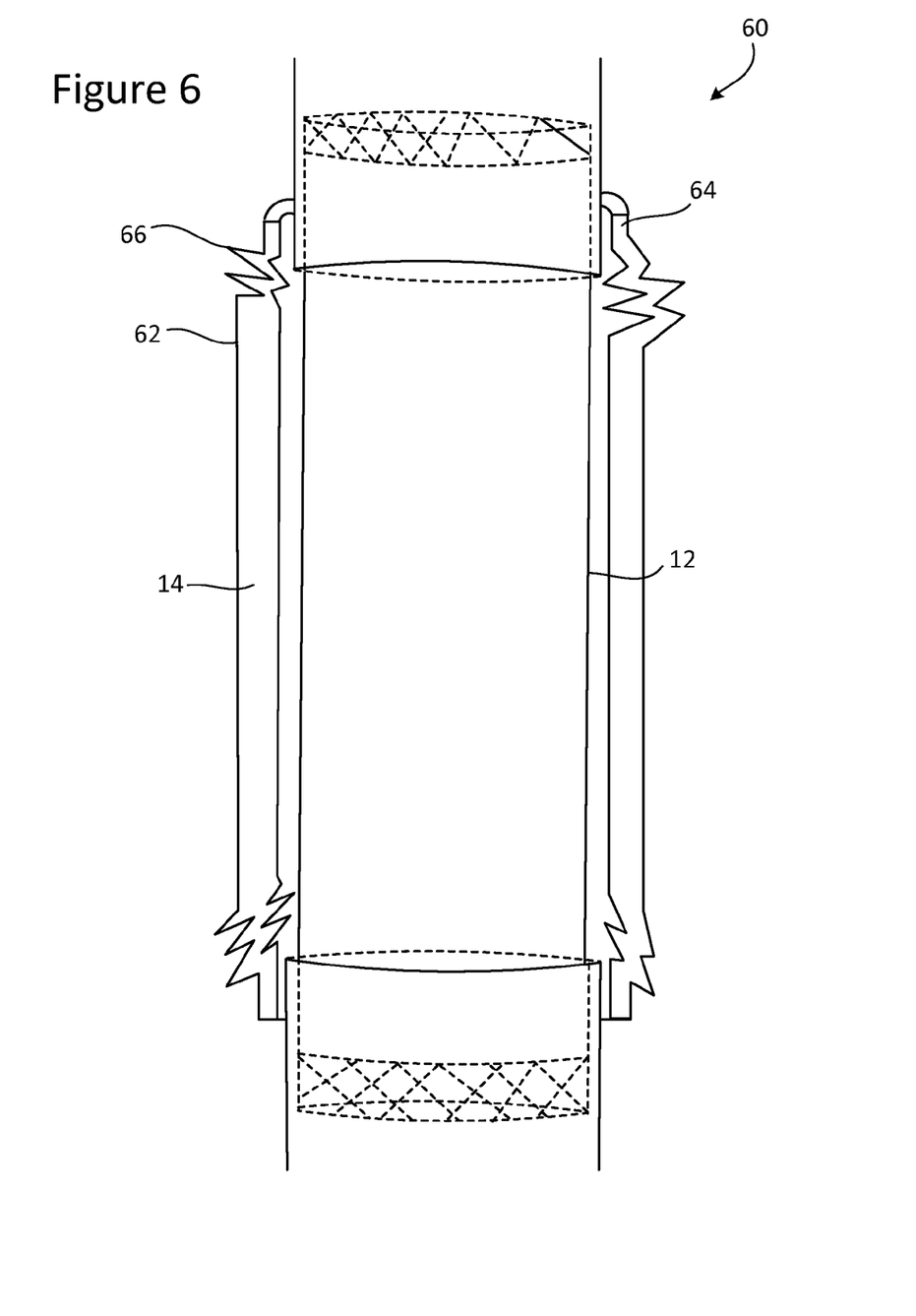
FIG. 6 is a side view of an esophageal replacement device having a thick outer layer in accordance to one embodiment provided herein. The forward portion of outer layer 14 is not shown to provide a better view of the other components.

With reference to FIG. 6, device 60 can include first layer 12 and second layer 14. Second layer 14 can include a center section 62 located between distal and proximal ends of second layer 14, an attachment section 64, and an extension 66. Center section 62 can be thicker than attachment section 64 and extension 66. Attachment section 64 can provide a location for sutures or clips. Extensions 66 can reduce the chance of leakage and/or prevent or reduce tension in order to maintain connection of second layer 14 to a stump end of an esophagus in case of contraction of one or both of the stump ends.

Figure 7:
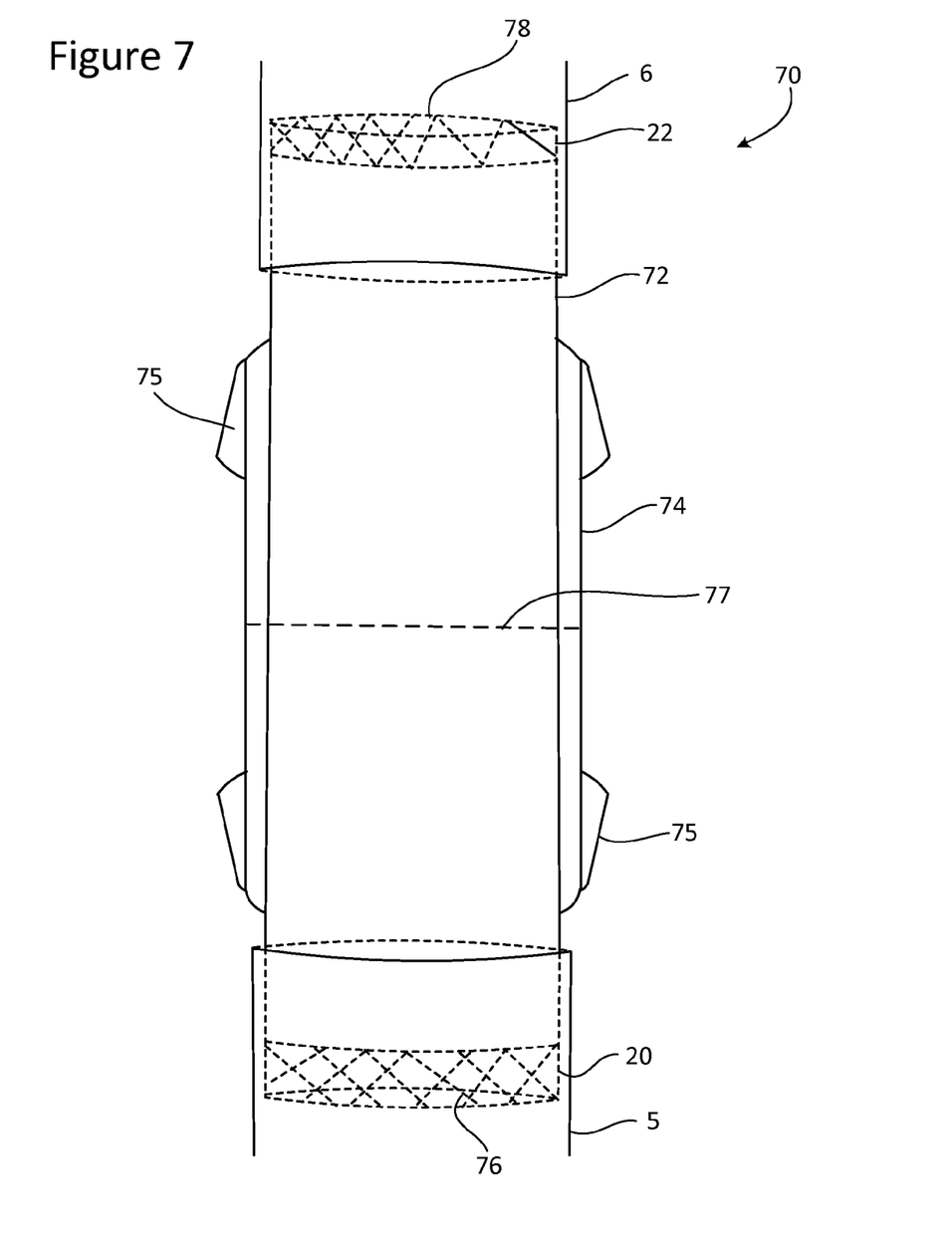
FIG. 7 is a side view of an esophageal replacement device in accordance to one embodiment provided herein. The forward portion of outer layer 14 is not shown to provide a better view of the other components.

With reference to FIG. 7, device 70 can include a first layer 72 and a second layer 74. Second layer 74 can include distal end section 75 and optionally, a center attachment point 77. End sections 75 of second layer 74 can be folded over, rolled, or clipped back onto itself to allow distal end regions 76 (lower) and 78 (upper) of first layer 72 to be exposed. Once distal end regions 76 and 78 have been deployed into distal stump ends 5 and 6, end sections 75 can be unfolded, unrolled, or unclipped to allow second layer 74 to be deployed over the distal stump ends.

In some cases, a device provided herein can include a mechanism to apply tension to pull one stump end of the esophagus toward another stump end of the esophagus to speed the healing process. For example, such a mechanism could be configured to incrementally reduce the distance between a distal stent ring and a proximal stent ring over time to stimulate more rapid cellular in-growth. In some cases, magnetic force can be used. In some cases, the tension can be applied endoscopically. In some cases, the tension can be applied remotely (e.g., pneumatic, current induction through coils, or battery-charged motor actuation). In some cases, telescoping action can shorten the length of struts (e.g., struts 32).

In some cases, a device provided herein can include a third layer (e.g., a sheath layer). Such a third layer can be configured to constrain the device for delivery in the desired location within the patient's body. During deployment, the third layer (e.g., sheath layer) can be pulled back enough to insert the first layer into the stump end and to allow exposure of the second layer, which could then be sutured to the mucosal layer of the stump. In some cases, the sheath layer can be divided into a proximal half and a distal half. For example, in surgical or thoracoscopic procedures, the distal half of the sheath can be used to insert the first layer into the distal stump and then released (e.g., unfurled, unclipped, untied, etc.). Likewise, the proximal half of the sheath can be used to insert the first layer into the proximal stump and then released.

In some cases, a device provided herein can include a second sheath layer (e.g., fourth layer) such that a first layer and a second layer are each constrained by separate sheaths. During deployment, the outer sheath (e.g., fourth layer) can be deployed outside the distal stump end and retracted to expose the second layer, which can then be sutured to the distal stump end. The third layer (e.g., inner sheath layer) can be deployed inside the distal stump end and can be pulled back to allow exposure of the ring stent end of the first layer, which can optionally be sutured to the stump.

In some cases, a device provided herein can include other constraining mechanisms in place of a sheath layer. For example, a stent or strut can be releasably restrained in a radially compressed state by a wire or thread woven through or around the ring stent structure. The wire or thread can be cut or pulled to deploy the ring stent structure. When the wire or thread is drawn taught, the ring stent structure can be restrained. When the wire or thread is released, the ring stent structure can expand automatically. In some cases, more than one wire or thread can be used. For example, in some cases, one wire can be used to constrain a proximal ring stent, one wire to constrain a distal ring stent, and another wire to optionally constrain the struts or rings. In some cases, one wire or thread can be used to constrain multiple stents and struts or rings. In some cases, the threads or wires can be color-coded or can contain other indicators for ease of removal.

In some cases, a second of a device provided herein may not be attached to (e.g., sutured to) the stump. For example, a first layer can be attached to the stump a few cm beyond the edge of the stump. In such cases, the second layer can be positioned in close proximity to the stump but free. In some cases, the second layer can be attached to the first layer, but not directly attached to the stumps.

In some cases, a device provided herein can include a second layer (e.g., an outer layer or biological layer) that includes struts and/or rings made of a porous graft material, mesh, polyethylene terephthalate (Dacron), steel, polymer, or other scaffold material that would allow cellular in-growth. In some cases, the struts and or rings can be made of a biodegradable or bioabsorbable material. In some cases, the struts and/or rings can be sandwiched between two layers of biologic material so they can be permanent fixtures. In such cases, the first layer (e.g., an inner layer) can lack struts.

In some cases, an inner surface of a first layer of a device provided herein can include a coating (e.g., a hydrophobic or slippery coating). Such a coating can be designed to promote food passage.

During use, a device provided herein can be implanted into a mammal (e.g., a human) to bridge a gap between two stumps of an esophagus. Surgical, thoracoscopic, endoscopic, or a combination of these procedures can be used. For example, a device provided herein can be implanted in a manner as shown in FIG. 1. Once cellular in-growth into a layer (e.g., a second layer) of the device occurs, the non-biological layers (e.g., a first layer) can be removed. For example, endoscopic surgery can be performed to remove a first layer from a human patient after a sufficient replacement esophagus section is generated within the patient.

For example, as shown in FIG. 7, a device provided herein can be placed surgically. A constrained distal ring stent end can be placed within the lumen of the distal stump end. The distal ring stent end of a first layer can be released by cutting a restraining wire or tie. The second layer can then be folded down over and sutured to the outer surface of the distal stump end. The constrained proximal ring stent of the first layer can be placed in the proximal stump end and unconstrained to release the proximal ring stent end within the lumen of the proximal stump end. The second layer can be unfolded over and attached to the outer surface of the proximal stump end.

In some cases, a device provided herein can be introduced orally (e.g., endoscopically) through the lumen of a proximal stump end of an esophagus. A delivery apparatus (e.g., third layer or sheath layer) can be used to deliver the device to the distal stump end. The delivery apparatus can be deployed into the lumen of the distal stump end and then be retracted to expose distal end region 16 and ring stent structure 20, such that ring stent structure 20 is no longer constrained and is deployed in the distal stump end. Ring stent structure 20 can optionally be sutured to the distal stump end. Further retraction of the delivery apparatus further exposes the first and second layer of the esophageal replacement device until the entire device is free of the deployment apparatus, and the proximal end region 18 and ring stent structure 22 are released into the proximal stump end. The delivery apparatus can then be removed transorally. Optionally, ring stent structure 22 can be sutured to the proximal stump end.

As shown in FIG. 2, a catheter or other appropriate delivery conduit can then be used to optionally fill struts 32 with cells and/or growth factors to aid the cellular in-growth process. After an appropriate amount of time has passed to allow sufficient cellular in-growth into the second layer, the first layer can be removed by an endoscopic procedure.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for replacing a circumferential segment of an esophagus removed from a mammal with an esophageal replacement device, wherein said esophageal replacement device comprises:
   (a) a first layer comprising a distal end region having a stent ring structure, a proximal end region having a stent ring structure, and a central region located between said distal end region and said proximal end region, wherein the lengths of said ring stent structures of said distal end region and said proximal end region are between about 10 mm and about 50 mm, and
   (b) a second layer located in an outer position relative to said first layer, wherein said second layer comprises a distal end portion and a proximal end portion,
   wherein said method comprises:
   (i) inserting a portion of said distal end region into a channel of a lower stump end of said esophagus such that at least said ring stent structure of said distal end region is completely inserted within said channel of said lower stump end,
   (ii) inserting a portion of said proximal end region into a channel of a upper stump end of said esophagus such that at least said ring stent structure of said proximal end region is completely inserted within said channel of said upper stump end,
   (iii) positioning at least a portion of said distal end portion over an outer surface of said lower stump end of said esophagus, and
   (iv) positioning at least a portion of said proximal end portion over an outer surface of said upper stump end of said esophagus.

2. The method of claim 1, wherein said mammal is a human.

3. The method of claim 1, wherein said method comprises suturing said distal end region to said lower stump end of said esophagus and suturing said proximal end region to said upper stump end of said esophagus.

4. The method of claim 1, wherein said method comprises removing said first layer from said mammal after cellular in-growth into said second layer occurs.

5. The method of claim 1, wherein said first layer is longer than said second layer.

* * * * *